(12) United States Patent
Keusenkothen et al.

(10) Patent No.: US 9,682,900 B2
(45) Date of Patent: *Jun. 20, 2017

(54) HYDROCARBON CONVERSION

(71) Applicant: ExxonMobil Chemical Patents Inc., Baytown, TX (US)

(72) Inventors: Paul F. Keusenkothen, Houston, TX (US); Juan D. Henao, Houston, TX (US); Abhimanyu O. Patil, Westfield, NJ (US); Guang Cao, Princeton, NJ (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 191 days.

This patent is subject to a terminal disclaimer.

(21) Appl. No.: 14/543,405

(22) Filed: Nov. 17, 2014

(65) Prior Publication Data

US 2015/0158792 A1  Jun. 11, 2015

Related U.S. Application Data

(60) Provisional application No. 61/912,901, filed on Dec. 6, 2013.

(30) Foreign Application Priority Data

Feb. 5, 2014  (EP) .................... 14153945

(51) Int. Cl.
*C07C 2/76* (2006.01)
*C07C 2/86* (2006.01)

(52) U.S. Cl.
CPC ............. *C07C 2/865* (2013.01); *C07C 2/76* (2013.01); *C07C 2/864* (2013.01); *C07C 2529/40* (2013.01); *C07C 2529/44* (2013.01); *C07C 2529/46* (2013.01); *C07C 2529/48* (2013.01)

(58) Field of Classification Search
None
See application file for complete search history.

(56) References Cited

U.S. PATENT DOCUMENTS

| | | |
|---|---|---|
| 3,700,585 A | 10/1972 | Chen et al. |
| 3,702,886 A | 11/1972 | Argauer et al. |
| 3,709,979 A | 1/1973 | Chu et al. |
| 3,832,449 A | 8/1974 | Rosinski et al. |
| 3,911,041 A | 10/1975 | Kaeding et al. |
| 3,928,483 A | 12/1975 | Chang et al. |
| 3,931,349 A | 1/1976 | Kuo |
| 4,016,218 A | 4/1977 | Haag et al. |
| 4,016,245 A | 4/1977 | Plank et al. |
| 4,046,825 A | 9/1977 | Owen et al. |
| 4,049,573 A | 9/1977 | Kaeding |
| 4,062,905 A | 12/1977 | Chang et al. |
| 4,076,842 A | 2/1978 | Plank et al. |
| 4,079,095 A | 3/1978 | Givens et al. |
| 4,079,096 A | 3/1978 | Givens et al. |
| 4,088,706 A | 5/1978 | Kaeding |
| 4,111,847 A | 9/1978 | Stiles |
| 4,138,440 A | 2/1979 | Chang et al. |
| RE29,948 E | 3/1979 | Dwyer et al. |
| 4,229,424 A | 10/1980 | Kokotailo |
| 4,234,231 A | 11/1980 | Yan |
| 4,439,409 A | 3/1984 | Puppe et al. |
| 4,440,871 A | 4/1984 | Lok et al. |
| 4,499,327 A | 2/1985 | Kaiser |
| 4,556,477 A | 12/1985 | Dwyer |
| 4,826,667 A | 5/1989 | Zones et al. |
| 4,873,067 A | 10/1989 | Valyocsik et al. |
| 4,954,325 A | 9/1990 | Rubin et al. |
| 5,012,029 A * | 4/1991 | Han ...................... C07C 2/84 568/910 |
| 5,236,575 A | 8/1993 | Bennett et al. |
| 5,250,277 A | 10/1993 | Kresge et al. |
| 5,336,825 A | 8/1994 | Choudhary et al. |
| 5,362,697 A | 11/1994 | Fung et al. |
| 5,370,851 A | 12/1994 | Wilson |
| 5,633,417 A | 5/1997 | Beck et al. |
| 5,675,047 A | 10/1997 | Beck et al. |
| 5,936,135 A | 8/1999 | Choudhary et al. |
| 6,077,498 A | 6/2000 | Cabanas et al. |
| 6,200,536 B1 | 3/2001 | Tonkovich et al. |
| 6,219,973 B1 | 4/2001 | Lafferty |
| 6,365,792 B1 | 4/2002 | Stapf et al. |
| 6,518,475 B2 | 2/2003 | Fung et al. |
| 6,756,030 B1 | 6/2004 | Rohde et al. |
| 7,014,807 B2 | 3/2006 | O'Brien |
| 7,015,369 B2 | 3/2006 | Hack et al. |

(Continued)

FOREIGN PATENT DOCUMENTS

| | | |
|---|---|---|
| CN | 101244969 | 8/2008 |
| EP | 0293032 | 7/1993 |

(Continued)

OTHER PUBLICATIONS

Chemical and Engineering News, 63(5), 27 (1985).
Chemistry Letters, 35 (2), 142-147, 2006.
Catalysis Letters, 28, 241-248 (1994).
Ghose, R. et al, Applied Catalysis A:General 452(2013) 147-154.
R.M. Navarro, M.A. Pena and J.L.G.Fierro, Chem. Rev., vol. 107, p. 3952, 2007.
V.R. Choudhary, A.K.Kinage and T.V.Choudhary, Science, vol. 275, pp. 1286-1288, 1997.

(Continued)

*Primary Examiner* — In Suk Bullock
*Assistant Examiner* — Philip Louie

(57) ABSTRACT

This disclosure relates to the conversion of methane to higher molecular weight ($C_{5+}$) hydrocarbon, including aromatic hydrocarbon, to materials and equipment useful in such conversion, and to the use of such conversion for, e.g., natural gas upgrading.

10 Claims, No Drawings

(56) References Cited

U.S. PATENT DOCUMENTS

| | | | |
|---|---|---|---|
| 7,022,888 | B2 | 4/2006 | Choudhary et al. |
| 7,453,018 | B2 | 11/2008 | Dakka et al. |
| 7,799,962 | B2 | 9/2010 | Dakka et al. |
| 7,977,519 | B2 | 7/2011 | Iaccino et al. |
| 8,119,076 | B2 | 2/2012 | Keusenkothen et al. |
| 8,138,384 | B2 | 3/2012 | Iaccino et al. |
| 8,552,247 | B2 | 10/2013 | Noe et al. |
| 2004/0192990 | A1* | 9/2004 | Choudhary ............... C07C 1/20 585/638 |
| 2005/0107481 | A1 | 5/2005 | Janssen et al. |
| 2006/0149109 | A1 | 7/2006 | Ruziska et al. |
| 2007/0161717 | A1 | 7/2007 | Hu et al. |
| 2007/0249879 | A1* | 10/2007 | Iaccino ..................... C07C 2/78 585/418 |
| 2007/0259972 | A1 | 11/2007 | Lattner et al. |
| 2008/0033218 | A1 | 2/2008 | Lattner et al. |
| 2008/0293980 | A1* | 11/2008 | Kiesslich ................. B01J 29/46 585/408 |
| 2010/0305221 | A1* | 12/2010 | Schunk ..................... C01B 3/46 518/704 |
| 2012/0083637 | A1 | 4/2012 | Clem et al. |
| 2013/0023709 | A1 | 1/2013 | Cizeron et al. |
| 2013/0253079 | A1 | 9/2013 | Jothimurugesan et al. |

FOREIGN PATENT DOCUMENTS

| | | |
|---|---|---|
| EP | 1704132 | 7/2005 |
| EP | 2184269 | 5/2010 |
| GB | 2191212 | 12/1987 |
| WO | 97/17290 | 5/1997 |
| WO | 2004/087624 | 10/2004 |
| WO | 2012/099674 | 7/2012 |

OTHER PUBLICATIONS

V.R. Choudhary and P. Devadas, Microporous and Mesoporous Materials, vol. 23, pp. 231-238, 1998.

J. Guo, H. Lou, H. Zhao, L.Zheng and X.Zheng, Journal of Molecular Catalysis A: Chemical, vol. 239, pp. 222-227, 2005.

J. Gou, H. Lou and X. Zheng, Journal of Natural Gas Chemistry, vol. 18, pp. 260-272, 2009.

O.A. Anunziata, G. A. Eimer and L.B.Pierella, Applied Catalysis A: General, vol. 190, pp. 169-176, 2000.

Alkhawaldeh Ammar et al.: "Conversion of mixtures of methane and ethylene or acetylene into liquids", Pre-Print Archive—Amer. Inst. of Chem Engr., Spring National Meeting, New Orleans, LA USA, Mar. 11-14, 2001 Proceedings of the Second Topical Conference on Natural Gas Utilization, American Institute of Chemical Engineer, Jan. 1, 2002(Jan. 1, 2002) p. 416 paragraph 3; figure 4.

XlAo-Song Li et al; "A process for a high yield of aromatics from the oxygen-free conversion of methane: combining plasma with Ni/HZSM-5 catalysts", Green Chemistry, vol. 9, No. 6, Jan. 1, 2007 (Jan. 1, 2007), p. 647, col. 2, last paragraph p. 650, col. 2, paragraph 1: figures 1-3.

V Ha: "Aromatization of methane over zeolite supported molybdenum: active sites and reaction mechanism", Journal of Molecular Catalysis A: Chemical, vol. 181, No. 1-2, Mar. 25, 2002, pp. 283-290.

Oscar A. Anunziata: Catalysis Letters, vol. 87, No. ¾, Jan. 1, 2003, 167-171.

"Conversion of biomass-derived syngas to alcohols and C2 oxygenates using supported Rh catalysts in a microchannel reactor", Jiami Hu, Yong Wang, Chusha Cao, Douglas C. Elliot, Don J. Stevens, James F. White, 1, Jan. 30, 2007, Catalysis Today vol. 120, pp. 90-95.

H. Yagita et al., Environmental Catalysis, G. Centi et al. Eds. SCI Publicaiton, Rome, 1995, pp. 639-642.

"Iron Particle Size Effects for Direct Production of Lower Olefins for Synthesis Gas", Hirsa M. Torres Galvis, Johannes H. Bitter, Thomas Davidian, Matthijs Ruitenbeek, A. Iulian Dugulan, and Krijn P. de Jong.s.l : Journal of American Chemical Society, Sep. 6, 2012, Journal of the American Chemical Society.

"Supported Iron Nanoparticles as Catalysts for Sustainable Production of Lower Olefins", Hirsa M. Torres Galvis, Johannes H. Bitter, Chaitanya B. Khare, Matthijs Ruitenbeek, A. Luian Dugulan, and Krijn P. de Jong, 335, Feb. 17, 2012, Science, vol. 6070, pp. 835-838.

"Heterogeneous Catalytic Synthesis of Ethanol from Biomass-Derived Syngas", James J. Spivey, Adefemi Egbebi, Mar. 7, 2007, Chemical Society Reviews, vol. 38, pp. 1514-1515.

"Ruthenium Melt Catalysis", Platinum Metals Review, Knifton, John 1985, vol. 29, p. 63-72.

Choudhary et al., Angew. Chem. Int. Ed. 2005, 44, 4381-4385.

J.R. Aderson, Appl. Catal. 47, (1989) 177.

J.S. Lee et al, Catal. Rev-Sci. Eng., 30 (1988) 249.

G.J. Hutchings et al., Chem Soc.Rev., 18 (1989) 25.

Science 153 (1966) 1393 "High Temperature Synthesis of Aromatics Hydrocarbons from Methane".

J.H. Lunsford, Ang Chem. Intl. Ed. Engl. 24 (1995), 970.

J. Haggin, Methane to Gasoline Plant Adds to New Zealand Liquid Fuel Resources, Chemical & Engineering News p. 22, Jun. 22, 1987.

J.H. Lunsford, The Catalytic Conversion of Methane to Higher Hydrocarbons, Catal. Today, vol. 6, p. 235, 1990.

Synthesis gas conversion utilizing mixed catalyst composed of CO reducing catalyst and solid acid: II. Direct syntheseis of aromatic hydrocarbons from synthesis gas. Kaoru Fujimoto, Yoshihiro Kudo, Hiro-o Tominaga. May 1984, Journal of Catalysis, vol. 87, is. 1, 136-143.

Selective Conversion of Methanol into Aromatic Hydrocarbons Over Silver Exchanged ZAM-5 Zeolites. Inoue, Yoshihiro, Nakashiro, Katsumi, Ono, Yoshio. S.L.: Elsevier; 1995, Microporous Materials, vol. 4, 379-383.

Sachchit Majhi et al. "Direct conversion of methane with methanol toward higher hydrocarbon over GA modified Mo/H-ZSM-5 catalyst", Journal of Industrial and Engineering Chemistry, vol. 20, No. 4, Oct. 14, 2013, pp. 2364-2369.

Anunziata O.A. et al: "Methane transformation into aromatic hydrocarbons by activiation with LPG over Zn-ZSM-11 Zeolite" Catalysis Letters, Springer New York LLC, United States, vol. 58, No. 4, Apr. 1, 1999, pp. 235-239.

Zhang, C-L et al: "Aromatization of Methane in the absence of oxygen over mo-based catalysts supported on different types of zeolites" , Catalysis Letters, vol. 56, No. 4, Jan. 1, 1999, 207-213.

Parisa Moghimpour Bijani et al: "nonoxidative Aromatization of CH 4 using C3H8 as a Coreactant: Thermodynamic and Experimental Analysis", Industrial and Engineering Chemistry Research, vol. 53, No. 2, Jan. 15, 2014, pp. 572-581.

Kondratenko, E.V. et al., Handbook of Heterogeneous Catalysis, vol. 6, (2008)3010-3023.

G. Centi, G. Cum, J.L.G. Fierro and J. M. Lopez Nieto, "Direct Conversion of Methane, Ethane, and Carbon Dioxide to Fuels and Chemicals", The Catalyst Group Resources Inc., Spring House, 2008.

\* cited by examiner

HYDROCARBON CONVERSION

CROSS REFERENCE TO RELATED APPLICATIONS

This application claims priority to U.S. Ser. No. 61/912,901, filed Dec. 6, 2013, the disclosure of which is incorporated herein by reference in its entirety. This application also claims priority to EP 14153945.2, filed Feb. 5, 2014. Cross reference is made to the following related patent applications: (i) P.C.T. Patent Application No. PCT/US2014/065947, filed Nov. 17, 2014; (ii) U.S. patent application Ser. No. 14/543,271, filed Nov. 17, 2014; (iii) P.C.T. Patent Application No. PCT/US2014/065961, filed Nov. 17, 2014; (iv) U.S. patent application Ser. No. 14/543,243, filed Nov. 17, 2014; (v) P.C.T. Patent Application No. PCT/US2014/065969, filed Nov. 17, 2014; (vi) U.S. patent application Ser. No. 14/543,426, filed Nov. 17, 2014; (vii) P.C.T. Patent Application No. PCT/US2014/065956, filed Nov. 17, 2014; and (viii) U.S. patent application Ser. No. 14/543,365, filed Nov. 17, 2014.

FIELD

This disclosure relates to the conversion of methane to higher molecular weight ($C_{5+}$) hydrocarbon, including aromatic hydrocarbon, to materials and equipment useful in such conversion, and to the use of such conversion for, e.g., natural gas upgrading.

BACKGROUND

Although methane is abundant, its relative inertness has limited its utility in conversion processes for producing higher-value hydrocarbon. For example, oxidative coupling methods generally involve highly exothermic and potentially hazardous methane combustion reactions, frequently require expensive oxygen generation facilities, and produce large quantities of environmentally sensitive carbon oxides. In addition, non-oxidative methane aromatization is equilibrium-limited, and temperatures ≥about 800° C. are needed for methane conversions greater than a few percent.

To obviate this problem, catalytic processes have been proposed for co-converting methane and one or more co-reactants to higher hydrocarbon, such as aromatics. For example, U.S. Pat. No. 5,936,135 discloses reacting methane at a temperature in the range of 300° C. to 600° C. with (i) a $C_{2-10}$ olefin and/or (ii) a $C_{2-10}$ paraffin in the presence of a bifunctional pentasil zeolite catalyst, having strong dehydrogenation and acid sites, to produce aromatics. The preferred mole ratio of olefin and/or higher paraffin to methane and/or ethane in the feed ranges from about 0.2 to about 2.0.

Other processes utilize organic oxygenate as a co-reactant for the non-oxidative methane conversion to produce higher hydrocarbon, including aromatics. For example, U.S. Pat. No. 7,022,888 discloses a process for the non-oxidative conversion of methane simultaneously with the conversion of an organic oxygenate, represented by a general formula: $CnH_2n+1OCmH_2m+1$, wherein C, H and O are carbon, hydrogen and oxygen, respectively; n is an integer having a value between 1 and 4; and m is an integer having a value between zero and 4. The methane and oxygenate are converted to $C_{2+}$ hydrocarbon, particularly to gasoline range $C_6$-$C_{10}$ hydrocarbon and hydrogen, using a bifunctional pentasil zeolite catalyst, having strong acid and dehydrogenation functions, at a temperature below 700° C.

However, since the co-reactants employed in the processes of the '135 and '888 patents are themselves valuable commodities, there is interest in developing alternative routes for the conversion of methane into aromatics and particularly routes that allow more methane to be incorporated into the aromatic product, and that operates over a broad molar ratio range of methane to co-reactant in the feed.

SUMMARY

It has been found that methane can be more efficiently converted to $C_{5+}$ hydrocarbon when the conversion is carried out in the presence of organic oxygenate and $C_{2+}$ aliphatic hydrocarbon. It is observed that including $C_{2+}$ aliphatic hydrocarbon with the methane and organic oxygenate results in a surprising increase in the yield of $C_{5+}$ hydrocarbon from the conversion. While not wishing to be bound by any theory or model, it is believed that the reaction is more efficient than prior art processes, which do not utilize a $C_{2+}$ aliphatic hydrocarbon co-reactant with the organic oxygenate, because the $C_{2+}$ aliphatic hydrocarbon assists the cyclization of methane fragments during the conversion reaction. Moreover, the reaction can be carried out efficiently at relatively low temperatures, e.g., ≤700° C., such as ≤300° C., over a broad range of methane to organic oxygenate molar ratio, e.g., in the range of from 0.6:1 to 20:1.

These findings have led to the development of processes for converting to $C_{5+}$ hydrocarbon a feed comprising $C_{2+}$ aliphatic hydrocarbon, $C_{1+}$ organic oxygenate, and at least 9 mole % of methane, the mole % being per mole of feed. The molar ratio of methane to $C_{1+}$ organic oxygenate in the feed is in the range of from 0.6:1 to 20:1 and the molar ratio of methane to $C_{2+}$ aliphatic hydrocarbon in the feed is in the range of from 0.1:1 to 20:1. The process includes contacting the feed with a catalyst comprising at least one molecular sieve and at least one dehydrogenation component under conditions, including a temperature ≤700° C., effective to convert at least part of the methane, $C_{2+}$ hydrocarbon, and $C_{1+}$ organic oxygenate in the feed to a product comprising at least 5 wt. % of $C_{5+}$ hydrocarbon, based on the weight of the product. At least a portion of the $C_{5+}$ hydrocarbon can be separated from the product and conducted away, e.g., for storage and/or further processing. The methane can be derived from natural gas, for example. The $C_{1+}$ organic oxygenate can be produced from syngas, with the syngas being optionally derived from natural gas. The $C_{2+}$ aliphatic hydrocarbon can be derived from natural gas, e.g., from the same natural gas from which the methane is derived. The natural gas can be a wet natural gas, such as shale gas.

When the methane and $C_{2+}$ aliphatic hydrocarbon are derived from natural gas, aspects of the invention provide a convenient method for natural gas upgrading. The closeness of atmospheric boiling points among methane and $C_{2+}$ aliphatic hydrocarbon in the natural gas leads to complications in separating one or more of these molecules, e.g., separating from the natural gas a portion of the methane for use as a reactant or fuel. Utilizing the present process for converting at least a portion of the $C_{2+}$ aliphatic hydrocarbon in the natural gas to $C_{5+}$ hydrocarbon having a significantly greater atmospheric boiling point considerably simplifies this separation problem. Instead of a relatively difficult methane separation from natural gas upstream of the process, unconverted methane can be more easily separated from the higher-boiling $C_{5+}$ hydrocarbon in the product downstream of the process. Reaction conditions can be adjusted to increase or decrease the amount of unconverted methane available for separation as desired.

It has also been found that utilizing an inorganic oxygenate in the methane conversion increases the efficiency of the reaction, obviating the need for a $C_{2+}$ aliphatic hydrocarbon co-reactant. It was believed that the formation of $C_{5+}$ hydrocarbon from methane, and particularly the production of aromatics from methane, would require an organic oxygenate co-reactant to produce $CH_x$ fragments. It has surprisingly been found that this is not the case. While not wishing to be bound by any theory or model, it is believed that sufficient hydrogen is made available to the reaction from the methane cracking, obviating the need for an organic oxygenate as a source of $CH_x$ fragments. In other words, it is believed that the chemistry is different from the case where organic oxygenate is utilized as the sole co-reactant. The inorganic oxygenate can be utilized in combination with organic oxygenate, e.g., at an organic oxygenate:inorganic oxygenate molar ratio in the range of 0.1 to 20, e.g., 2 to 10, such as 3 to 10. The inorganic oxygenate can be utilized in combination with $C_{2+}$ aliphatic hydrocarbon, e.g., at a $C_{2+}$ aliphatic hydrocarbon:inorganic oxygenate molar ratio in the range of 0.1 to 20, e.g., 2 to 10, such as 3 to 10. In certain aspects, the inorganic oxygenate is utilized with both organic oxygenate and $C_{2+}$ aliphatic hydrocarbon.

These findings have led to the development of processes for converting to $C_5+$ hydrocarbon a feed comprising $C_{1+}$ inorganic oxygenate and ≥9 mole % methane, the mole percent being per mole of feed. The molar ratio of methane to $C_{1+}$ inorganic oxygenate in the feed is in the range of from 0.6:1 to 20:1. The process includes contacting the feed with a catalyst comprising at least one molecular sieve and at least one dehydrogenation component under conditions, including a temperature ≤700° C., effective to convert at least part of the methane and the $C_{1+}$ inorganic oxygenate in the feed to a product comprising at least 5 wt. % of $C_{5+}$ hydrocarbon, based on the weight of the product. At least a portion of the $C_{5+}$ hydrocarbon can be separated from the product and conducted away, e.g., for storage and/or further processing. Optionally, the feed has a molar ratio of molecular hydrogen to $C_{1+}$ inorganic oxygenate in the range of from 0.5:1 to 20:1. The molecular hydrogen and $C_{1+}$ inorganic oxygenate can be derived from syngas, for example. The methane can be derived for natural gas, for example.

DETAILED DESCRIPTION

Definitions

For the purpose of this description and appended claims the following terms are defined. The term "Cn" hydrocarbon wherein n is a positive integer, e.g., 1, 2, 3, 4, or 5, means a hydrocarbon having n number of carbon atom(s) per molecule. The term "Cn+" hydrocarbon wherein n is a positive integer, e.g., 1, 2, 3, 4, or 5, as used herein, means a hydrocarbon having at least n number of carbon atom(s) per molecule. The term "Cn−" hydrocarbon wherein n is a positive integer, e.g., 1, 2, 3, 4, or 5, as used herein, means a hydrocarbon having no more than n number of carbon atom(s) per molecule. The term "aromatics" means hydrocarbon molecules containing at least one aromatic core. The term "hydrocarbon" encompasses mixtures of hydrocarbon, including those having different values of n. The term "organic oxygenate" means molecules having the formula $CnH_{2n+1}OCmH_{2m+1}$, wherein C, H and O are carbon, hydrogen and oxygen, respectively; n is an integer having a value ≥1, e.g., in the range of from 1 to 4; and m is an integer having a value ≥zero, e.g., in the range of from zero to 4. Examples of organic oxygenate include one or more of methanol, ethanol, dimethyl ether, and diethyl ether. The term "inorganic oxygenate" means oxygenate molecules that do not satisfy the specified formula for organic oxygenate. A Cn oxygenate molecule contains n carbon atoms, where n is an integer ≥1. This term encompasses mixtures of carbon-containing oxygenate molecules having different molecular weights and/or different values of n. Examples of $C_{1+}$ inorganic oxygenate include one or more of aldehyde, carbon monoxide, and carbon dioxide. The term "syngas" means a mixture comprising ≥12 mole % molecular hydrogen and ≥0.4 mole % carbon monoxide, the mole percents being per mole of the mixture.

As used herein, the numbering scheme for the groups of the Periodic Table of the Elements is as disclosed in Chemical and Engineering News, 63(5), 27 (1985).

The present disclosure relates to a process for the production of $C_{5+}$ hydrocarbon, particularly aromatics from feeds containing methane. In certain aspects, the feed comprises methane, $C_{1+}$ organic oxygenate, and $C_{2+}$ aliphatic hydrocarbon, such as $C_{2+}$ alkane. In other aspects, the feed comprises methane, $C_{1+}$ inorganic oxygenate, and optionally (i) $C_{2+}$ aliphatic hydrocarbon and/or (ii) $C_{1+}$ organic oxygenate. Representative feeds will now be described in more detail. The invention is not limited to these feeds, and this description is not meant to foreclose other feeds within the broader scope of the invention.

Feeds Comprising Methane, Organic Oxygenate, and $C_{2+}$ Aliphatic Hydrocarbon

In certain aspects, the feed comprises ≥9 mole % of methane, e.g., ≥25 mole %, such ≥40 mole %; $C_{1+}$ organic oxygenate; and $C_{2+}$ aliphatic hydrocarbon; wherein (i) the molar ratio of methane to $C_{1+}$ organic oxygenate in the feed is in the range of from 0.6:1 to 20:1, such as from 4:1 to 10:1, for example from 5:1 to 10:1; and (ii) the molar ratio of $C_{2+}$ aliphatic hydrocarbon to $C_{1+}$ organic oxygenate in the feed is in the range of from 0.1:1 to 20:1 such as from 2:1 to 10:1, for example from 3:1 to 10:1. The mole percents are based on per mole of feed. Generally, at least a portion of the feed is in the vapor phase during the conversion. For example, ≥75.0 wt. %, e.g., ≥90.0 wt. %, such as ≥99.0 wt. % of the feed can be in the vapor phase during the conversion, the weight percents being based on the weight of the feed. Examples of suitable feeds comprise from 40 mole % to 80 mole % of methane, from 1 mole % to 15 mole % acetylene, and from 1 mole % to 40 mole % $C_{2+}$ aliphatic hydrocarbon, the mole percents being per mole of feed. The remainder of the feed, if any, can comprise diluent, for example.

The methane can be obtained from natural gas, for example. Although separate sources of methane and $C_{2+}$ aliphatic hydrocarbon can be utilized, one preferred source of these feed components is wet natural gas, that is natural gas containing some or all of the higher hydrocarbon, particularly $C_2$ to $C_5$ hydrocarbon, co-produced with methane. A particularly preferred source of natural gas is shale gas. In this way, the complex and costly process of separating methane from the higher hydrocarbon present in natural gas can be simplified and the natural gas can be converted to easily transport liquid hydrocarbon.

In certain aspects, the $C_{1+}$ organic oxygenate comprises a compound represented by a general formula: $CnH_{2n+1}OCmH_{2m+1}$, wherein C, H and O are carbon, hydrogen and oxygen, respectively; n is an integer having a value from 1 to 4, e.g., from 1 to 3, such as 1 or 2; and m is an integer having a value from zero to 3, e.g., from zero to 2, such as zero or 1. Examples of suitable $C_{1+}$ organic oxygenate include methanol, ethanol, dimethyl ether, diethyl ether, dipropyl ether, dibutyl ether, methyl ethyl, ether, methyl propyl ethers, methyl butyl ethers, and mixture thereof. Preferred $C_{1+}$ organic oxygenate includes methanol, ethanol, dimethyl ether, diethyl ether, and mixtures thereof. In certain aspects, the $C_{1+}$ organic oxygenate comprises ≥90.0 wt. % of $C_1$ to $C_4$ alcohol and/or $C_2$ to $C_8$ dialkyl ether, based on the weight of the $C_{1+}$ organic oxygenate, e.g., ≥90.0 wt. % of methanol, ethanol, dimethyl ether, diethyl ether and mixtures thereof.

In certain aspects, the organic oxygenate is methanol produced from natural gas via syngas. The syngas can comprise, e.g., molecular hydrogen and ≥5.0 wt. % of carbon monoxide, based on the weight of the syngas, and the syngas can have an $H_2$:($CO+CO_2$) molar ratio in the range of from 0.5 to 20, e.g., an $H_2$:CO molar ratio in the range of from 0.5 to 20, e.g., 0.6 to 4.

The syngas can be produced by any convenient method, including conventional methods such as the partial oxidation of methane and/or the steam reforming of methane. Suitable methods include those described in U.S. Patent Application Publication Nos. 2007/0259972 A1, 2008/0033218 A1, and 2005/0107481, each of which is incorporated by reference herein in its entirety.

Syngas can be produced, e.g., by contacting methane with steam in the presence of a catalyst, such as one or more metals or compounds thereof selected from Groups 7 to 10 of the Periodic Table of the Elements supported on an attrition resistant refractory support, such as alumina. The contacting is normally conducted at high temperature, such as from 800° C. to 1100° C., and pressures up to 5000 kPa such that the stream converts the methane to carbon monoxide and hydrogen according to reactions, such as:

$$CH_4 + H_2O = CO + 3H_2.$$

Steam reforming is energy intensive in that the process consumes over 200 kJ/mole of methane consumed. A more preferred process of producing syngas is therefore is partial oxidation, in which the methane is burned in the presence of a catalyst and in an oxygen lean environment to produce carbon monoxide and hydrogen, according to the following representative reaction:

$$CH_4 + \tfrac{1}{2}O_2 \rightarrow CO + 2H_2.$$

It will be appreciated that steam reforming produces syngas with a molar ratio of $H_2$:CO of about 3:1, whereas the product of the partial oxidation of methane has a $H_2$:CO of about 2:1. The $H_2$:CO molar ratio of the syngas is not critical and in fact aspects of the invention utilizing syngas having an $H_2$:CO molar ratio <2.0, e.g., <1.5, or even <1.1.

In certain aspects, the syngas is catalytically converted to organic $C_{1+}$ oxygenate, e.g., $C_{1+}$ alcohol, such as methanol. The conversion of syngas to methanol can be carried out at very high selectivity's using a mixture of copper, zinc oxide, and alumina at a temperature of 200° C. to 400° C. and pressures of 50-500 atm. In addition to Cu/ZnO/$Al_2O_3$, other catalyst systems suitable for methanol synthesis include Zn/V$Cr_2O_3$, Cu/ZnO, Cu/ZnO/$Cr_2O_3$, Cu/Th$O_2$, Co$S_x$, Mo$S_x$, Co—Mo$S_x$, Ni—$S_x$, Ni—Mo$S_x$, and Ni—Co—Mo$S_x$.

Besides methane and organic oxygenate, the feed can further comprise $C_{2+}$ aliphatic hydrocarbon. In certain aspects, the $C_{2+}$ aliphatic hydrocarbon comprises $C_{2+}$ alkane, such as $C_2$ to $C_5$ alkane. For example the $C_{2+}$ aliphatic hydrocarbon can comprise ≥50.0 wt. % of $C_2$ to $C_5$ alkane, based on the weight of the $C_{2+}$ aliphatic hydrocarbon, e.g., ≥75.0 wt. %, such as ≥90.0 wt. %, or ≥99.0 wt. %.

Another suitable source of methane and $C_{2+}$ aliphatic hydrocarbon is product obtained from the oxidative conversion of methane to ethylene and higher hydrocarbon ("OCM"). OCM is a process in which methane is reacted with an oxygen-containing gas in the presence of a catalyst, such as an alkaline earth/rare earth metal oxide catalyst, such as Sr-promoted $La_2O_3$, at a temperature of 600° C. to 800° C. and a pressure is 1 to 10 bars. The reaction is described in, for example, U.S. Pat. No. 5,336,825, the entire contents of which are incorporated herein by reference. The process couples the methane into higher hydrocarbon, such as ethylene, by reactions such as:

$$2CH_4 + O_2 \rightarrow C_2H_4 2H_2O.$$

In the process, methane is activated heterogeneously on the catalyst surface, forming methyl free radicals, which then couple in the gas phase to form ethane, which subsequently undergoes dehydrogenation to form ethylene. The process is accompanied by the non-selective reaction of methyl radicals and oxygen in the gas phase to produce carbon monoxide and carbon dioxide. The product of the OCM reaction is therefore a mixture comprising $C_{2+}$ aliphatic hydrocarbon, water, CO, $CO_2$ and residual oxygen and methane. The methane and/or $C_{2+}$ aliphatic hydrocarbon can be separated from the OCM product and utilized as feed components with the $C_{1+}$ organic oxygenate.

This approach significantly lessens disadvantages encountered in operating conventional OCM processes, in that the need to separate $C_2/C_3$ olefins at low concentration from the OCM product is avoided, while the $C_2/C_3$ olefins are converted to less volatile $C_{5+}$ hydrocarbon which can be more easily separated from the methane. Other OCM by-products, such as residual oxygen, CO and/or $CO_2$ can be separated from the OCM product and utilized as feed for one or more syngas processes, e.g., to produce syngas utilized for synthesizing the $C_{1+}$ organic oxygenate.

Yet another suitable source of methane and $C_{2+}$ aliphatic hydrocarbon is the product of the non-catalytic pyrolysis of methane in the presence of a limited oxygen environment to produce $C_{2+}$ aliphatic hydrocarbon such as ethylene and/or propylene. Such a process is described in, for example, in International Patent Publication No. WO 2012/099674A2, which is incorporated by reference herein in its entirety. The product is a complex mixture comprising $C_{2+}$ aliphatic hydrocarbon (primarily ethylene, propylene and higher hydrocarbon), water, CO, $CO_2$ and residual methane. The methane and/or desired $C_{2+}$ aliphatic hydrocarbon can be separated from the product and utilized as feed components with the $C_{1+}$ organic oxygenate.

Besides methane, organic oxygenate, and $C_{2+}$ aliphatic hydrocarbon, the feed can further comprise diluent. Optionally, the feed further comprises ≥0.1 mole % diluent, based on per mole feed. Diluent generally comprises species which do not react in significant amounts with methane and/or organic oxygenate to produce $C_{5+}$ hydrocarbon under the specified operating conditions. Suitable diluent includes one or more of molecular hydrogen; hydrogen sulfide, and molecular nitrogen. In certain aspects, the feed comprises diluent in an amount in the range of from 0.1 mole % to 50 mole %, based on per mole of feed. Where present, some or all of the diluent can be present as by-products of the process used to produce the feed's methane and/or organic oxygenate.

Feeds Comprising Methane and Inorganic Oxygenate

In certain aspects, the feed comprises $C_{1+}$ inorganic oxygenate, and ≥9 mole % of methane, e.g., ≥25 mole %, such ≥40 mole %, wherein the molar ratio of methane to $C_{1+}$ inorganic oxygenate in the feed is in the range of from 0.6:1 to 20:1, such as from 5:1 to 15:1, for example from 7:1 to 10:1. The mole percents are based on per mole of feed. Generally, at least a portion of the feed is in the vapor phase during the conversion. For example, ≥75.0 wt. %, e.g., ≥90.0 wt. %, such as ≥99.0 wt. % of the feed can be in the vapor phase during the conversion, the weight percents being based on the weight of the feed. Optionally, the feed further comprises molecular hydrogen. The feed can have, e.g., a molecular hydrogen:$C_{1+}$ inorganic oxygenate molar ratio ≥0.6, e.g., ≥1.0, such as ≥10.0. In certain aspects, the feed has a molecular hydrogen:$C_{1+}$ inorganic oxygenate molar ratio in the range of from 0.5:1 to 20:1, e.g., 0.6:1 to 20:1.

Optionally, the methane is obtained from natural gas, e.g., wet natural gas. The same natural gas sources can be utilized as specified for feeds containing $C_{1+}$ organic oxygenate.

The $C_{1+}$ inorganic oxygenate can comprise, e.g., one or more of CO, $CO_2$ and formaldehyde. For example, the $C_{1+}$ inorganic oxygenate can comprise ≥50.0 wt. % of CO, based on the weight of the $C_{1+}$ inorganic oxygenate, such as ≥75.0 wt. %, or ≥90.0 wt. %, or ≥99.0 wt. %. Optionally, balance of $C_{1+}$ inorganic oxygenate, if any, can be $CO_2$. The feed can have, e.g., a molecular hydrogen:(CO+$CO_2$) molar ratio ≥0.6, e.g., ≥1.0, such as ≥10.0, or in the range of from about 0.6 to about 20. In certain aspects, the $C_{1+}$ inorganic oxygenate is substantially all CO. The feed can have, e.g., a molecular hydrogen:CO molar ratio ≥0.6, e.g., ≥1.0, such as ≥10.0, or in the range of from about 0.6 to about 20. Optionally, the molecular hydrogen:CO molar ratio is ≥4, such as in the range of from 1 to 4.

In certain aspects, (i) the $C_{1+}$ inorganic oxygenate comprises CO and (ii) the CO is obtained from syngas. The syngas can comprise, e.g., molecular hydrogen and ≥5.0 wt. % of carbon monoxide, based on the weight of the syngas. The syngas can have an $H_2$:(CO+$CO_2$) molar ratio in the range of from 0.5 to 20, e.g., in the range of from 0.6 to 4, such as an $H_2$:CO molar ratio in the range of from 0.6 to 4. The syngas can be produced by any convenient method, including conventional methods such as those specified in connection with feeds containing $C_{1+}$ organic oxygenate. As in the case of those feeds, methane for syngas generation can be obtained, e.g., from natural gas.

Another suitable source of methane, C1+ inorganic oxygenate and C2+ aliphatic hydrocarbon is OCM product. Since OCM product comprises unconverted methane, $C_{2+}$ aliphatic hydrocarbon, and $C_{1+}$ inorganic oxygenate (primarily CO and $CO_2$), the OCM product can be utilized directly as a feed for the instant process for converting methane to $C_{5+}$ hydrocarbon such as aromatics, utilizing the specified catalyst. The OCM product alone can be fed to the specified conversion step or can be combined with additional methane, $C_{1+}$ inorganic oxygenates, molecular hydrogen, and/or $C_{2+}$ hydrocarbon. Similarly the product of the non-catalytic pyrolysis of methane, as specified for feeds containing $C_{1+}$ organic oxygenates, can be conducted to the specified conversion reaction for producing the $C_{5+}$ hydrocarbon. The pyrolysis product alone can be fed to the specified conversion step or can be combined with additional methane, $C_{1+}$ inorganic oxygenate, molecular hydrogen, and/or $C_{2+}$ hydrocarbon.

Optionally, the feed further comprises ≥0.1 mole % diluent, based on per mole of feed. Diluent generally comprises species which do not react in significant amounts with methane and/or $C_{1+}$ inorganic oxygenate to produce $C_{5+}$ hydrocarbon under the specified operating conditions. Suitable diluent includes one or more of molecular hydrogen, hydrogen sulfide, and molecular nitrogen. In certain aspects, the feed comprises diluent in an amount in the range of from 0.1 mole % to 50 mole %, based on per mole of feed. Where present, some or all of the diluent can be present as by-products of the process used to produce the feed's methane and/or $C_{1+}$ inorganic oxygenate.

Converting the Feed to $C_{5+}$ Hydrocarbon

In certain aspects, the invention relates to processes which include contacting the feed with a bi-functional catalyst comprising at least one molecular sieve and at least one dehydrogenation component to produce a product comprising ≥5.0 wt. % of aromatics based on the weight of the product. The process can be carried out over a broad range of methane:oxygenate molar ratio, and can be carried out efficiently at a temperature that is significantly below that utilized in prior art processes. Although the mechanisms of the reactions occurring in the present process are not fully understood, it is believed that the methane is activated by the $C_{1+}$ oxygenate at the metal and acid sites of the bi-functional catalyst allowing the methane and, where present, the $C_{2+}$ aliphatic hydrocarbon, to be aromatized at temperatures below 700° C., e.g., at a temperature ≤300° C. Whereas the non-oxidative aromatization of methane is thermodynamically restrained at low temperatures and the aromatization of $C_{1+}$ oxygenates is highly exothermic, the present process couples the simultaneous endothermic conversion of methane and the exothermic aromatization of the $C_{1+}$ oxygenate, rendering the process highly energy efficient. The process can utilize one or more catalysts, e.g., at least one bi-functional catalyst. Representative bi-functional catalysts contain at least one acidic functionality (generally provided by the molecular sieve component) and at least one dehydrogenation functionality (generally provided by the dehydrogenation metal component). Certain catalysts useful in the invention will now be described in more detail. The invention is not limited to these catalysts, and this description is not meant to foreclose other catalysts within the broader scope of the invention.

In certain aspects, the catalyst comprises at least one medium pore size molecular sieve having a Constraint Index of 2-12 (as defined in U.S. Pat. No. 4,016,218). Examples of such medium pore molecular sieves include ZSM-5, ZSM-11, ZSM-12, ZSM-22, ZSM-23, ZSM-35, ZSM-48 and mixtures and intermediates thereof. ZSM-5 is described in detail in U.S. Pat. No. 3,702,886 and Re. 29,948. ZSM-11 is described in detail in U.S. Pat. No. 3,709,979. A ZSM-5/ZSM-11 intermediate structure is described in U.S. Pat. No. 4,229,424. ZSM-12 is described in U.S. Pat. No. 3,832,449. ZSM-22 is described in U.S. Pat. No. 4,556,477. ZSM-23 is described in U.S. Pat. No. 4,076,842. ZSM-35 is described in U.S. Pat. No. 4,016,245. ZSM-48 is more particularly described in U.S. Pat. No. 4,234,231. Optionally, the molecular sieve is one comprising at least one set of pores of substantially uniform size extending through the molecular sieve, wherein geometric mean of the cross-sectional dimensions of each of the pores is >5 Å, or >5.3 Å, e.g., ≥5.4 Å such as ≥5.5 Å, or in the range of 5 Å to 7 Å, or 5.4 Å to 7 Å.

In other aspects, the catalyst employed in the present process comprises at least one molecular sieve of the MCM-22 family. As used herein, the term "molecular sieve of the MCM-22 family" (or "material of the MCM-22 family" or "MCM-22 family material" or "MCM-22 family zeolite") includes one or more of:

(i) molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference;

(ii) molecular sieves made from a common second degree building block, being a 2-dimensional tiling of such MWW framework topology unit cells, forming a monolayer of one unit cell thickness, preferably one c-unit cell thickness;

(iii) molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and (iv) molecular sieves made by any regular or random 2-dimensional or 3-dimensional combination of unit cells having the MWW framework topology.

Molecular sieves of the MCM-22 family include those molecular sieves having an X-ray diffraction pattern including d-spacing maxima at 12.4±0.25, 6.9±0.15, 3.57±0.07 and 3.42±0.07 Angstrom. The X-ray diffraction data used to characterize the material are obtained by standard techniques using the K-alpha doublet of copper as incident radiation and a diffractometer equipped with a scintillation counter and associated computer as the collection system.

Materials of the MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO 97/17290), MCM-36 (described in U.S. Pat. No. 5,250,277), MCM-49 (described in U.S. Pat. No. 5,236,575), MCM-56 (described in U.S. Pat. No. 5,362,697), and mixtures thereof. Related zeolite UZM-8 is also suitable for use as a molecular sieve component of the present catalyst.

In certain aspects, the molecular sieve employed in the present process may be an aluminosilicate or a substituted aluminosilicate in which part of all of the aluminum is replaced by a different trivalent metal, such as gallium or indium.

The invention can be practiced using catalysts that have been subjected to one or more catalyst treatments, e.g., selectivation. For example, the catalyst can comprise at least one molecular sieve which has been selectivated, either before introduction of the catalyst into the reactor or in-situ in the reactor, by contacting the catalyst with a selectivating agent, such as at least one organosilicon in a liquid carrier and subsequently calcining the catalyst at a temperature of 350° C. to 550° C. This selectivation procedure can be repeated two or more times and alters the diffusion characteristics of the catalyst such that the formation of para-xylene over other xylene isomers is favored. Such a selectivation process is described in detail in U.S. Pat. Nos. 5,633,417 and 5,675,047, the entire contents of which are incorporated herein by reference.

In addition to the molecular sieve component, the catalyst generally comprises at least one dehydrogenation component, e.g., at least one dehydrogenation metal. The dehydrogenation component is typically present in an amount of at least 0.1 wt. %, such as from 0.1 to 5 wt. %, of the overall catalyst. The dehydrogenation component can comprise one or more neutral metals selected from Groups 3 to 13 of the Periodic Table of the Elements, such as Ga, In, Zn, Cu, Re, Mo, W, La, Fe, Ag, Pt, Pd, and/or one or more oxides, sulfides and/or carbides of these metals. The dehydrogenation component can be provided on the catalyst in any manner, for example by conventional methods such as impregnation or ion exchange of the molecular sieve with a solution of a compound of the relevant metal, followed by conversion of the metal compound to the desired form, namely neutral metal, oxide, sulfide and/or carbide. Part or all of the dehydrogenation metal may also be present in the crystalline framework of the molecular sieve. A carbonyl conversion functionality can also be used when the co-reactant comprises inorganic oxygenate, e.g., one or more of Cu, Co, Cr, Fe, Mo, Zn, such as in one or more of metal, oxide, sulfide, etc.

In one aspect, the bi-functional catalyst used in the present process is selected from the group consisting of Ga and/or In-modified ZSM-5 type zeolites such as Ga and/or In-impregnated H-ZSM-5, Ga and/or In-exchanged H-ZSM-5, H-gallosilicate of ZSM-5 type structure and H-galloaluminosilicate of ZSM-5 type structure. These zeolites can also be prepared by any suitable method, including conventional methods.

For example, the bi-functional catalyst may contain tetrahedral aluminum and/or gallium, which is present in the zeolite framework or lattice, and octahedral gallium or indium, which is not present in the zeolite framework but present in the zeolite channels in close vicinity to the zeolitic protonic acid sites, and which is attributed to the presence of tetrahedral aluminum and gallium in the catalyst. The tetrahedral or framework Al and/or, Ga is responsible for the acid function of the catalyst and octahedral or non-framework Ga and/or In is responsible for the dehydrogenation function of the catalyst. In one preferred aspect, the bi-functional catalyst comprises H-galloaluminosilicate of ZSM-5 type structure having framework (tetrahedral) Si/Al and Si/Ga mole ratios of about 10:1 to 100:1 and 15:1 to 150:1, respectively, and non-framework (octahedral) Ga of about 0.5 to 0 wt. %.

In addition to the molecular sieve components and dehydrogenation component, the catalyst may be composited with another material which is resistant to the temperatures and other conditions employed in the conversion reaction. Such materials include active and inactive materials and synthetic or naturally occurring zeolites as well as inorganic materials such as clays and/or oxides such as alumina, silica, silica-alumina, zirconia, titania, magnesia or mixtures of these and other oxides. The latter may be either naturally occurring or in the form of gelatinous precipitates or gels including mixtures of silica and metal oxides. Clays may also be included with the oxide type binders to modify the mechanical properties of the catalyst or to assist in its manufacture. Use of a material in conjunction with the molecular sieve, i.e., combined therewith or present during its synthesis, which itself is catalytically active may change the conversion and/or selectivity of the catalyst. Inactive materials suitably serve as diluents to control the amount of conversion so that products may be obtained economically and orderly without employing other means for controlling the rate of reaction. These materials may be incorporated into naturally occurring clays, e.g., bentonite and kaolin, to improve the crush strength of the catalyst under commercial operating conditions and function as binders or matrices for the catalyst. The relative proportions of molecular sieve and inorganic oxide matrix vary widely, with the sieve content ranging from about 1 to about 90 percent by weight and more usually, particularly, when the composite is prepared in the form of beads, in the range of about 2 to about 80 weight percent of the composite.

Process Conditions

In certain aspects, the invention relates to processes which include contacting the feed with one or more of the specified bi-functional catalysts, e.g., those comprising at least one molecular sieve and at least one dehydrogenation component, to produce a product comprising ≥5.0 wt. % of aromatics based on the weight of the product. Selected process conditions for the conversion will now be described in more detail. The invention is not limited to these process conditions, and this description is not meant to foreclose other process conditions within the broader scope of the invention.

In certain aspects, conversion of the feed comprising methane and co-reactants to aromatic hydrocarbon is generally conducted at a temperature less than 700° C., such as from 250° C. to 699° C. and a pressure in the range of from 1 bar (absolute) to 5 bar (absolute) (100 to 500 kPa absolute). Space velocity is not critical, and the conversion conditions can include, e.g., a gas hourly space velocity a feed gas hourly space velocity of ≥100 cm$^3$/h/g of catalyst. The conversion process can be conducted in one or more fixed bed, moving bed or fluidized bed reaction zones. The conversion can be operated, e.g., continuously, semi-continuously, or in batch mode.

In certain aspects, the conversion conditions include exposing the specified feed in the presence of at least one specified catalyst to a temperature in the range of from 275° C. to 650° C., e.g., 300° C. to 600° C., such as 325° C. to 550° C. The conversion conditions can further include a pressure in the range of from 1.2 bar (abs) to 4 bar (abs), and a feed gas hourly space velocity in the range of 100 cm$^3$/h/g of catalyst to 10,000 cm$^3$/h/g of catalyst, e.g., 500 cm$^3$/h/g of catalyst to 5000 cm$^3$/h/g of catalyst.

When operated utilizing the specified feed, in the presence of at least one of the specified catalysts, and with the specified conversion conditions, the products of the conversion are mainly $C_{5+}$ hydrocarbon, water, and lesser amounts of ethylene, ethane, propylene, propane and $C_4$ hydrocarbon. For example, the product of the conversion can comprise, e.g., (i) ≥5.0 wt. % of $C_{5+}$ hydrocarbon, e.g., ≥10.0 wt. %, such as ≥15 wt. %; (ii) and ≤10.0 wt. % $C_2$ to $C_4$ hydrocarbon, e.g., 5.0 wt. %, such as ≥1.0 wt. %; the weight percents being based on the weight of the product. Methane conversion is generally ≥5.0 wt. %, based on the weight of methane in the feed, e.g., ≥10.0 wt. %, such as ≥15.0 wt. %. The $C_{5+}$ hydrocarbon comprises mainly aromatics, e.g., ≥50.0 wt. % of $C_6$ to $C_{10}$ aromatics, based on the weight of the product's $C_{5+}$ hydrocarbon, such as ≥75.0 wt. %, or ≥90.0 wt. %, or ≥95.0 wt. %. For example, the molar ratio of aromatic hydrocarbon produced to methane converted is generally ≥3.5:1, such as ≥4:1.

The $C_6$ to $C_{10}$ aromatics can readily be removed from the product by any convenient method, e.g., by one or more conventional fractionation and extraction techniques.

All patents, test procedures, and other documents cited herein, including priority documents, are fully incorporated by reference to the extent such disclosure is not inconsistent and for all jurisdictions in which such incorporation is permitted.

While the illustrative forms disclosed herein have been described with particularity, it will be understood that various other modifications will be apparent to and can be readily made by those skilled in the art without departing from the spirit and scope of the disclosure. Accordingly, it is not intended that the scope of the claims appended hereto be limited to the examples and descriptions set forth herein but rather that the claims be construed as encompassing all the features of patentable novelty which reside herein, including all features which would be treated as equivalents thereof by those skilled in the art to which this disclosure pertains.

When numerical lower limits and numerical upper limits are listed herein, ranges from any lower limit to any upper limit are contemplated, and are expressly within the scope of the invention. The term "comprising" is synonymous with the term "including". Likewise whenever a composition, an element or a group of components is preceded with the transitional phrase "comprising", it is understood that we also contemplate the same composition or group of components with transitional phrases "consisting essentially of," "consisting of", "selected from the group consisting of," or "is" preceding the recitation of the composition, component, or components, and vice versa.

The invention claimed is:

1. A process for producing $C_{5+}$ hydrocarbon, the process comprising:
   (a) providing a feed comprising a $C_{1+}$ inorganic oxygenate and ≥9 mole % of methane, per mole of feed, wherein a molar ratio of methane to $C_{1+}$ inorganic oxygenate is in a range of 0.6:1 to 20:1, and wherein the $C_{1+}$ inorganic oxygenate comprises aldehyde;
   (b) contacting the feed with a catalyst comprising at least one molecular sieve and at least one dehydrogenation component under conditions, including a temperature less than 700° C., effective to convert at least a portion of the methane and at least a portion of the aldehyde in the feed to a product comprising at least 5 wt. % of $C_{5+}$ hydrocarbons based on the weight of the product, wherein the $C_{5+}$ hydrocarbons comprise $C_6$ to $C_{10}$ aromatics; and
   (c) separating at least part of the $C_{5+}$ hydrocarbons from the product.

2. The process of claim 1, wherein the molar ratio of methane to $C_{1+}$ inorganic oxygenate in the feed is in the range of from 5:1 to 15:1.

3. The process of claim 1, wherein the $C_{1+}$ inorganic oxygenate further comprises CO added to the feed as syngas, and wherein the syngas has a molecular hydrogen to CO molar ratio ≤4.

4. The process of claim 3, wherein at least a portion of the syngas is produced by partial oxidation of methane.

5. The process of claim 1, wherein the temperature is less than 600° C., and the feed further comprises $C_{2+}$ aliphatic hydrocarbons and/or molecular hydrogen, and wherein the $C_{2+}$ aliphatic hydrocarbons comprise one or more $C_2$ to $C_5$ alkanes.

6. The process of claim 5, wherein the feed further comprises $C_{1+}$ organic oxygenates, and wherein the $C_{1+}$ organic oxygenates comprise $C_1$ to $C_4$ organic oxygenates.

7. The process of claim 1, wherein the feed comprises ≥25 mole % of methane.

8. The process of claim 1, wherein (i) the molecular sieve comprises an aluminosilicate and/or a gallosilicate, and wherein the molecular sieve has an average pore size of 5.4 Å to 7 Å, and (ii) the dehydrogenation component comprises a metal or compound thereof from Groups 3 to 13 of the Periodic Table.

9. The process of claim 1, wherein the temperature of step (b) is ≤300° C., and the contacting conditions of step (b) further comprises a pressure in the range of from 1.2 bar (absolute) to 4 bar (absolute) and/or a feed gas hourly space velocity of ≥100 cm$^3$/h/g of catalyst.

10. The process of claim 1, wherein (i) the product comprises, ≤10.0 wt. % $C_2$ to $C_4$ hydrocarbons, based on the weight of the product, (ii) methane conversion is ≥5.0 wt. %, based on the weight of methane in the feed, and (iii) the $C_{5+}$ hydrocarbons comprise ≥90.0 wt. % of $C_6$ to $C_{10}$ aromatics, based on the weight of the $C_{5+}$ hydrocarbons.

\* \* \* \* \*